United States Patent [19]

Frisbee

[11] Patent Number: 4,970,081
[45] Date of Patent: Nov. 13, 1990

[54] CONTROLLED-RELEASE, LOW-DOSE ASPIRIN FORMULATION AND METHOD OF TREATING VASCULAR OCCLUSIVE DISEASE THEREWITH

[75] Inventor: Steven E. Frisbee, Town of New Scotland, Albany County, N.Y.

[73] Assignee: Sterling Drug Inc., New York, N.Y.

[21] Appl. No.: 293,832

[22] Filed: Jan. 3, 1989

[51] Int. Cl.⁵ .......................... A61K 9/32; A61K 9/14; A61K 9/36
[52] U.S. Cl. ...................................... 424/480; 424/81; 424/482; 424/494; 424/497
[58] Field of Search ............... 424/482, 480, 479, 474, 424/494, 497, 81

[56] References Cited

U.S. PATENT DOCUMENTS

| | | | |
|---|---|---|---|
| 4,244,941 | 1/1981 | Lerk | 424/21 |
| 4,308,251 | 12/1981 | Dunn et al. | 424/19 |
| 4,351,825 | 9/1982 | Sothmann et al. | 424/19 |
| 4,361,545 | 11/1982 | Powell et al. | 424/19 |
| 4,389,393 | 6/1983 | Schor et al. | 424/19 |
| 4,666,705 | 5/1987 | DeCrosta et al. | 424/81 |
| 4,713,248 | 12/1987 | Kjrnaes et al. | 424/468 |
| 4,716,041 | 12/1987 | Kjrnaes et al. | 424/468 |
| 4,728,513 | 3/1988 | Ventouras | 424/461 |
| 4,784,858 | 11/1988 | Ventouras | 424/468 |
| 4,860,087 | 1/1989 | Mehta | 424/497 |

FOREIGN PATENT DOCUMENTS 0213083 3/1987 European Pat. Off. .
0250648 1/1988 European Pat. Off. .

OTHER PUBLICATIONS

Reilly and FitzGerald, "Presystemic Inhibition of Platelet Thromboxane Formation by Simulated, Slow Release, Low Dose Aspirin in Man", *Clinical Research* 32, 320A (1984).

Jakubowski et al., "Low—Dose Enteric—Coated Aspirin: A Practical Approach to Continuous—Release Low—Dose Aspirin and Presystemic Acetylation of Human Platelet Cyclooxygenase", *J. Lab. Clin. Med.* 108, 616–621 (1986).

Bochner and Lloyd, "Is There an Optimal Dose and Formulation of Aspirin to Prevent Arterial Thrombo—Embolism in Man", *Clinical Science* 71, 625–631 (1986).

Hennig and Kala, "Einfluss der Löslichkeit von Arzneistoffen auf ihre Freigabe aus mit Polymethacrylaten lackierten Retardpellets", *Pharmazie* 41, 814–815 (1986), Derwent Ringdoc Abst. 87—07956.

*Primary Examiner*—Thurman K. Page
*Attorney, Agent, or Firm*—Philip E. Hansen; Paul E. Dupont

[57] ABSTRACT

An aqueous-based formulation for coating aspirin granules to provide granules that may be compressed into tablets and that show approximately zero-order release kinetics for release rates of 5 to 15 mg/hour over a period extending five to eight hours is provided. The coating formulation preferably consists of an acrylate/-methacrylate copolymer, hydroxypropylmethylcellulose, sodium chloride and talc. A film-coated tablet comprised of the coated granules, filler granules, excipients, binders and disintegrants is also provided, as are processes for preparing the tablets and granules and methods for their use in the treatment of vascular occlusive diseases.

21 Claims, 3 Drawing Sheets

CONTROLLED-RELEASE, LOW-DOSE ASPIRIN FORMULATION AND METHOD OF TREATING VASCULAR OCCLUSIVE DISEASE THEREWITH

BACKGROUND OF THE INVENTION

1. Field of the Invention

This invention relates to a water-based formulation and a process for coating aspirin granules that results in coated granules that may be compressed into tablets and that release aspirin with approximately zero-order kinetics over a period extending five to eight hours. The invention further relates to rapidly disintegrating tablets comprising said coated aspirin granules, a process for the manufacture of said tablets, and a method of using said tablets for the prevention and treatment of human vascular occlusive diseases. Specifically the invention relates to processes for and products from the coating of aspirin granules with a neutral, insoluble but permeable, elastic film and the fashioning of tablets from said coated granules by compressing with disintegrants, antiadherents, lubricants and preferentially-crushable granules.

2. Information Disclosure

It is known in the art that aspirin significantly decreases platelet adhesiveness by acetylating cyclooxygenase in platelets. This biochemical action manifests itself in statistically significant protection from vascular occlusive events among patients given oral aspirin. It is also known that, at the doses given in most clinical trials, aspirin inhibits endothelial cyclooxygenase. Because the effects in these two tissues are believed to antagonize one another, there has been a search for a dose and dosage form of aspirin that might be effective in suppressing the production of thromboxane $B_2$(TX) by platelets without suppressing the production of prostacyclin (PC) by endothelial cells.

More recently Reilly and FitzGerald [*Clinical Research* 32, 320A(1984)] have suggested that if hepatic extraction were virtually complete with low doses of aspirin, repeated administration of low doses might permit cumulative presystemic inhibition of TX while protecting endothelial cyclooxygenase from exposure to aspirin. They reported that 1 mg of aspirin given every 30 minutes for 10 hours to human volunteers resulted in a decrease in serum TX by 66% at 10 hours while urinary PC was unaltered. Similarly, Jakubowski et al [*J. Lab. Clin. Med.* 108, 616–621(1986)] reported that granular, enteric-coated aspirin, when given three times a day in 27 mg doses to human volunteers, resulted in 96% inhibition of serum TX generation without detectable levels of aspirin in the systemic circulation. Formal clinical trials with low-dose, slow-release aspirin to treat or prevent transient ischemic attacks, myocardial infarction and related vascular occlusive events were suggested by Bochner and Lloyd [Clin. Sci. 71, 625–631 (1986)].

Until my discovery, no low-dose, controlled-release formulation for aspirin was known. Methods and formulations in the literature have suggested ways that one might approach the problem, but none of them addresses the five parallel requirements that I believe are necessary for large scale production and ultimate commercial distribution to the patient population: (1) A dosage form must provide a controlled, linear, near-zero-order release of low doses of aspirin; the release should be relatively independent of pH so that drug release is not governed by the pH changes that occur during gastrointestinal transit. (2) The components of the dosage form, including any coatings and films, must not interact or alter with time; the rate of release and total dose released must be unaffected by the conditions or duration of normal storage. (3) The dosage form should be in the form of a tablet to avoid the hazards of tampering that are associated with capsules. (4) The final dosage form must have minimal residence time in the stomach to avoid the gastric irritation associated with aspirin. (5) The process used to prepare the dosage form cannot utilize non-aqueous solvents, which require extensive and expensive mitigation measures to avoid environmentally unsatisfactory or hazardous conditions, but the aqueous process must not compromise the stability of the water-sensitive aspirin.

Thus, for example, Sothmann and Marttila (U.S. Pat. No. 4,351,825) describe a sustained-release, water-based system using an acrylate/methacrylate copolymer for coating tabletable granules of 50 mg of phenylpropanolamine hydrochloride and 100 mg of verapamil hydrochloride but there is no indication that the medication is released with zero-order kinetics nor is any duration longer than 3 hours demonstrated. The process is not described in detail, but it does not appear applicable to water-sensitive medicaments such as aspirin. Further, monolithic (also known as matrix) tablets are produced and the problem of gastric residence time is thus not addressed.

Dunn and Lampard (U.S. Pat. No. 4,308,251) describe 650 mg and 800 mg aspirin tablets that exhibit zero-order release in vitro and closely approximate zero-order absorption in vivo, but the tablets are monolithic and the disintegration times shown in the patent are all greater than two hours; the problem of gastric residence time is unrecognized. Further, the medicament tablets are prepared "by dissolving the release controlling agent in suitable organic solvent or solvent mixture such as methylene chloride and denatured alcohol [1:1(v/v)]. Other suitable solvents include but are not limited to, lower aliphatic alcohols such as methanol, isopropanol, n-propanol, etc., acetone and lower aliphatic ketones, such as methylethylketone, chloroform, carbon tetrachloride, ethyl acetate and nonchlorinated hydrocarbons."

Seth (European Application No. 250,648) describes a multiple unit dosage form of ibuprofen in which microspheres of ibuprofen are coated with Eudragit ® E30D ethyl acrylate/methyl methacrylate copolymer, and compressed into tablets containing not less than 600 mg of ibuprofen. The tablets release ibuprofen at an approximately zero-order rate for a period of ten hours; the tablets are said to release a flow of microspheres continuously into the intestines from the stomach and this flow is said to be largely independent of the subsequent emptying of the stomach; the coated microspheres are said to display their retard-effect throughout the entire duration of transit. The technique for preparing the microspheres requires mixing an aqueous mixture of ibuprofen, microcrystalline cellulose, carboxymethylcellulose and hydroxypropylmethylcellulose, putting the resulting mixture through an extruder and a spheronizer and drying the resulting spheres at 45° C. This is a process that is not feasible with water-sensitive medicaments such as aspirin; in the case of aspirin the amount of salicylic acid formed by hydrolysis during this process would be expected to fall well outside the allowed limits. Seth then describes a process of spray-coating a layer of pure Eudragit ®E30D. This process, while manageable when the particles have been deliberately made into hard microspheres, cannot be practiced on irregular granules such as aspirin on a commercial scale. Further Seth does not address the unique problems of low-dose dosage forms; the application states that the need which Seth's discovery satisfies is for a dosage form which contains higher doses than 300 or 400 mg. (page 2, line 17–20). Seth also does not address the question of long-term stability of the release rate.

Schor et al. (U.S. Pat. No. 4,389,393) describe 650 mg aspirin tablets that use hydroxypropylmethylcellulose to provide zero-order release with a duration of 8 hours, and without need for a solvent. However, the lowest release rate described in 65 mg per hour and the tablets are monolithic. It is well known to persons familiar with the art that release rate, tablet size, tablet shape, and dose of medicament have a complex relationship monolithic tablets; thus a 650 mg matrix tablet cannot be reduced to a 40 to 100 mg dose without unpredictably altering the release rate—perhaps even precluding zero-order release. Accordingly, I have observed that no combination of HPMC and ethylcellulose could be coated on aspirin granules to provide tabletable granules with a zero-order release rate of 5–15 mg/hr. When the HPMC/ethylcellulose ratio was adjusted to produce the proper release rate, the coating did not survive compression, and the resulting tablets produced an unacceptable, large, initial burst of aspirin. Additionally, Schor does not recognize the problem of gastric residence time.

Lerk (U.S. Pat. No. 4,244,941) describes a constant-release composition which produces tablets, requires no solvent, and provides a linear release rate approximating zero-order over a period up to five hours. However, the composition only works with highly water-soluble medicaments. Sulfanilamide, which is twice as soluble as aspirin, is the least soluble medicament for which an example is provided, and its release rate is impractically slow. (4.5 mg per hour).

Powell and Patel (U.S. Pat. No. 4,361,545) delineate the importance of zero-order release, and describe a tablet composition that provides zero-order release over periods of 5 to 8 hours for medicaments having the solubility properties of aspirin. The zero-order release depends upon a phenomenon of controlled surface erosion in a monolithic tablet and no tablets containing less than 300 mg of active ingredient are described. Thus, neither the problem of gastric residence time nor the problem of scale down to low-dose is addressed.

Hennig and Kala [*Pharmazie* 41, 814–815 (1986)] describe the coating of aspirin granules of 1.07 mm with an aqueous dispersion of Eudragit ®E30D and PEG 6000. The resulting particles have a zero-order release rate of 7.16 mg per hour over a period up to 8 hours; however, at 8 hours only 30 to 40% of the aspirin has been released, and there is no indication that the granules so produced could be compressed into a tablet.

Ventouras (European Application No. 213083) describes tablets containing 320 and 860 mg of a compound of methylxanthine medicaments in granules coated with Eudragit ®E30D, compressed with tableting aids, and coated with Eudragit ®E30D, lactose, talc, polysorbate and optionally with pigments. The tablets show zero-order release of methylxanthines over a period of 8 hours. Ventouras indicates that the tablet coating may be modified to control permeability by the inclusion of other water soluble fillers in place of the lactose of the example. Such water-soluble fillers discussed on page [3 paragraph 4] include: "Sodium chloride or a sugar, particularly lactose, fructose or D-mannit, [sic] or sorbitol or polyvinylpyrrolidone or a derivative thereof, or dextrane [sic] compounds of different molecular weight; or a swellable filler, e.g. hydroxypropylmethylcellulose, hydroxyethylcellulose or hydroxypropylcellulose, e.g. Pharmacoat ®-603, or an antisticking agent, e.g. talcum, or an emulsifier, e.g. polysorbate (Tween ®-80), or a coloring pigment, e.g. indigotin lake or a metal oxide, e.g. iron oxide, such as red iron oxide or yellow iron oxide, or titanium dioxide; or a plasticiser, e.g. polyethylene glycol, such as Lutrol E-400 (BASF)." Since he is not administering aspirin, Ventouras does not address the problems of gastric residence time, and a tablet coated with E30D will remain a monolith. The problem of extending the technology to administer low doses is unappreciated: in fact the release curves for the 2 doses (FIGS. 2 and 3 of EP Application No. 213083) indicate a drop in total medicament delivered from about 85% at the 860 mg dose to about 70% at the 320 mg dose.

Kjrnaes and Linnemann (U.S. Pat. No. 4,713,248) describe the coating of potassium chloride crystals in a fluid bed process with Eudragit ®E30D, hydroxypropylmethylcellulose and talc. The resulting coated particles may be compressed into tablets to provide tablets that release the same percent of medicament as the coated particles at one hour, indicating that the particles were compressed without substantial fracture of the control-release coating. Kjrnaes and Linnemann also recognize the problem of storage stability, but do not address it with a singlecoat particle. They describe a heat treating process which imparts storage stability and provides tablets with approximately zero-order release kinetics up to six hours; however, the particles that are heat treated have a second coating of HPMC and talc applied over the Eudragit ® coat. A second patent (U.S. Pat. No. 4,716,041) also to Kjrnaes et al. states (column 6, line 31 to 35 and line 53 to 59) in reference to coatings containing Eudragit ®E30D, HPMC, talc and optionally a hydrophobic substance: "In most cases, it has been found that, when subjected to the elevated temperatures necessary to obtain the effect desired above, the inner film layer tends to become tacky (adhesive) causing an undesirable agglomeration of the units. . . In both instances, ie. both when the substance incorporated in the coating and when the film-forming agent itself causes adhesion, it is therefore, necessary to provide the units with an additional, protective layer which is composed of a substance or a mixture of substances which is anti-adhesive at elevated temperatures and, preferably, also imparts flowability to the coated units." And, in fact, I have observed that if sodium chloride is deleted from the formulation of the present invention, the aspirin granules coated only with Eudragit ®, HPMC, and talc tend to agglomerate in the fluid bed coating process even in the absence of additional heat for curing.

Ventouras (U.S. Pat. No. 4,728,513) describes heat-treated granules of a compound of methylxanthine medicaments coated with a 6:1 mixture of ethyl acrylate/methyl methacrylate copolymer (Eudragit ®E30D) and ethylcellulose (Aquacoat ®ECD-30) followed by a top coat of ethylcellulose. The granules are stable, the release rate being essentially unaffected by storage 1 month at 35° C. and only slightly depressed by storage 1 month at 50° C. The granules are compressed into tablets by the use of conventional technology, utilizing art-known fillers, binders, disintegrants, and lubricants. The resulting tablets disintegrate very rapidly and release methylxanthines at approximately zero-order for 8 hours; however, only about 65% of the 900 mg dose is released by 8 hours.

Thus until my invention no one had addressed the problem of efficiently achieving controlled release (5 to 15 mg/hr for 8 hours) of aspirin from a low-dose tablet. Further, the systems described in the prior art that provide essentially zero-order, 5 to 8 hour release for non-aspirin medicaments cannot be extended to the aspirin problem without violating one or more of the requirements satisfied by my invention.

All of the systems described in the prior art that have been applied to aspirin sought stable, non-irritating, or sustained release of doses larger than 300 mg. Sustained-release products generally attempt to generate constant blood levels of a therapeutic agent from one administration of the agent to the next. The focus of my invention is not sustained release, but controlled release. According to my invention, the systemic blood levels of aspirin do not rise above 100 ng/mL at any time during the medication cycle. The duration of release of aspirin is of concern to my invention only indirectly in that it is a dependent variable resulting from the interplay of two required parameters: (1) the total dose must be sufficient to acylate a therapeutically useful proportion of platelet thromboxane synthetase, and (2) the rate of release must be low enough to allow virtually complete presystemic clearance.

SUMMARY OF THE INVENTION

In a composition of matter aspect, this invention relates to an aqueous-based formulation for coating aspirin granules to provide coated granules that may be compressed into tablets and that show approximately zero-order release kinetics over a period extending 5 to 8 hours. The release kinetics of said granules are substantially unchanged by six month's storage at room temperature, three month's storage at 40° C., or three months' storage at 40° C. and 75% relative humidity.

In a further composition aspect, the invention relates to aspirin granules of 0.5 to 1.5 mm particle size coated with 10 to 35%, preferably about 20%, on a dry weight basis, of a formulation containing a methyl methacrylate/ethyl acrylate copolymer, hydroxpropylmethylcellulose (HPMC), sodium chloride, and talc.

In a further composition aspect, the invention relates to rapidly disintegrating, low-dose, controlled-release aspirin tablets containing 40 to 100 mg of aspirin coated to provide a near zero-order release rate of about 5 to about 15 mg per hour for a period extending 5-8 hours.

In a process aspect, the invention relates to a process for preparing near-zero-order, controlled-release aspirin granules that may be compressed into tablets. The process does not utilize organic solvents.

In a further process aspect, the invention relates to a process for preparing low-dose, rapidly-disintegrating, controlled-release aspirin tablets. The tablets incorporate the coated aspirin granules described above along with such other excipients, binders, lubricants, diluents, glidants, plasticizers, film coatings, tableting aids, and disintegration enhancers as may be needed so that said tablets provide a release rate of about 5 to about 15 mg per hour.

In a method aspect, the invention relates to a method for treating or preventing vascular occlusive diseases in humans which comprises orally administering a tablet described above.

DESCRIPTION INCLUSIVE OF PREFERRED EMBODIMENTS

Figure 1:
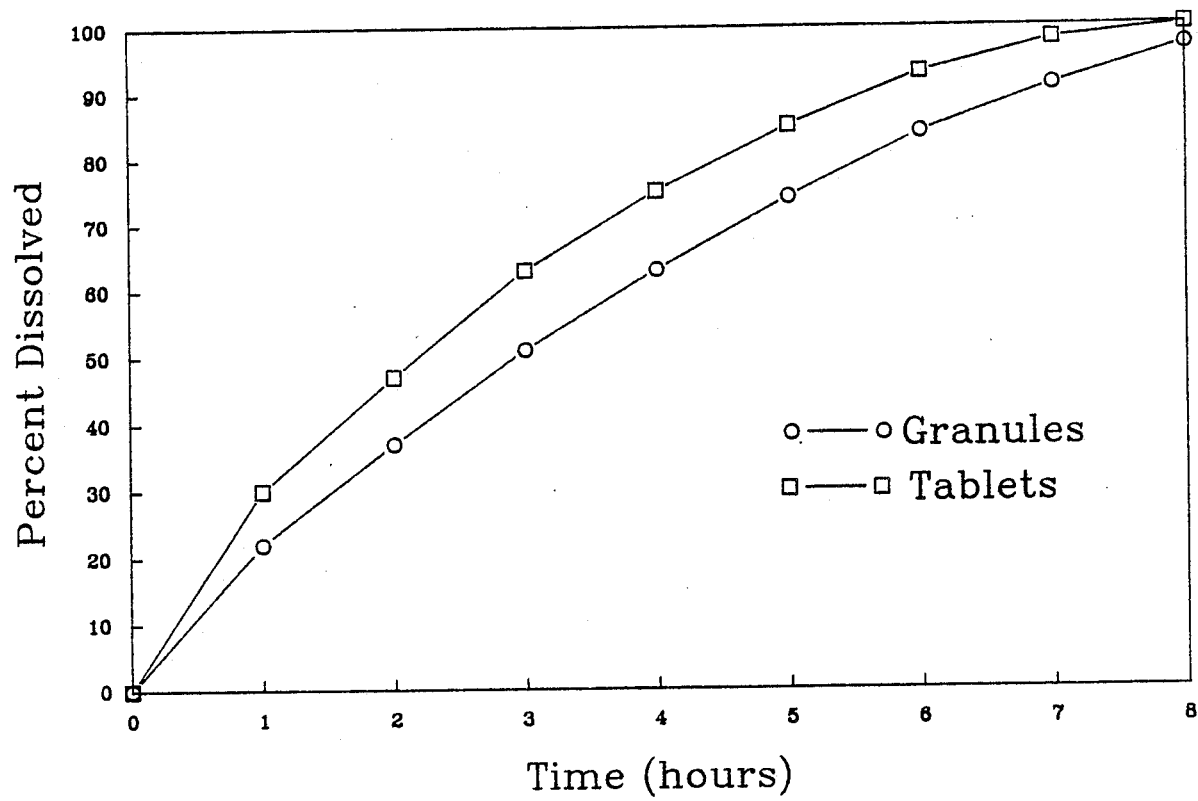
FIG. 1 shows the release of aspirin in percent of the total dose plotted against the time in hours for the granules of Example 1 and the tablets of Example 2.

In a composition aspect, the invention resides in an aqueous based formulation for coating aspirin granules to provide coated granules that may be compressed into tablets and that show approximately zero-order release kinetics for release rates of 5 to 15 mg/hr over a period extending 5 to 8 hours. The formulation consists essentially of (a) from about 40 to about 60 parts of a 70:30 copolymer of ethyl acrylate and methyl methacrylate of average molecular weight 800,000; (b) from about 10 to about 20 parts of USP 2910 hydroxypropylmethyl cellulose of ASTM viscosity 3 to 15 cps(c) from about 1 to about 12 parts of sodium chloride; (d) from about 20 to about 45 parts of talc USP and (e) from about 200 to about 900 parts of water.

A preferred embodiment of the coating formulation consists of about 48 parts of acrylate copolymer, about 16 parts of hydroxypropylmethylcellulose, about 3.2 parts of sodium chloride, about 32 parts of talc and about 396 parts of water. The acrylate/methacrylate copolymer is commercially available as a 30% aqueous dispersion from Rohm Pharma GmbH, Darmstadt (Federal Republic of Germany) under the name Eudragit ®NE30D (formerly known as E30D). The preferred hydroxypropylmethylcellulose carries the USP designation 2910 6 cps which indicates 28–30% methoxyl groups, 7–12% hydroxypropoxy groups, and an average molecular weight such that a 2% aqueous solution has a viscosity of 6 cps at 20° C. A hydroxypropylmethylcellulose which meets this criterion is available from the Dow Chemical Company (U.S.A.) as Methocel ®E and from Shin-etsu Limited (Japan) as Pharmacoat ® 606. The talc of the preferred embodiment has a median particle size of 3 μm and is available from Cypruss Industrial Minerals Company (U.S.A.) as Al-talc ®500.

In a further composition aspect, the invention resides in a controlled-release aspirin granule of particle size 0.5 to 1.5 mm coated with 10 to 35%, preferably about 20%, on a dry weight basis, of a formulation containing from about 40 to about 60, preferably about 48, parts of a 70:30 copolymer of ethyl acrylate and methyl methacrylate of average molecular weight 800,000 from about 10 to about 20, preferably about 16, parts of USP 2910 HPMC, preferably of 3–15 cps viscosity, most preferably of 6 cps viscosity, from about 1 to about 12, preferably about 3.2 parts of sodium chloride and from about 20 to about 45, preferably about 32, parts of talc USP, preferably of particle size 3 μm.

The function of the acrylate/methacrylate copolymer is to provide a permeable, but insoluble, shell that is unaffected by pH, that does not chemically interact with aspirin, and that will limit the rate of dissolution of aspirin. Its low glass transition temperature provides deformability. It can be applied in an aqueous-based spray coating operation. Other polymers having those properties would provide acceptable equivalents. The HPMC could, in principle, be replaced by any water-soluble, hydrophilic polymer to modulate the release of aspirin through the acrylate/methacrylate coat. Sodium chloride appears to function both as a permeability enhancer for the polymeric coat and as an aid to processing in the fluid bed technique used to coat granules; as such it prevents agglomeration of the fluid bed. Other water-soluble, pharmacologically innocuous salts would function in place of sodium chloride provided that they form crystalline inclusions in the polymer coat. Although talc is preferred to reduce tackiness and provide bulk, many pharmacologically innocuous, water-insoluble, anti-adhesive coating aids and pigments are known in the art: colloidal silicon dioxide, iron oxide, titanium dioxide etc.

In a further composition aspect, the invention resides in a rapidly disintegrating, low-dose, controlled-release aspirin tablet containing from 40 to 100 mg of aspirin coated as above and such other excipients, binders, glidants, lubricants, diluents, plasticizers, film coatings, tableting aids, and disintegration enhancers as may be needed to maintain the release rate of about 5 to about 15 mg per hour and to provide a disintegration time of less than 15 minutes. To produce such a tablet, I have found it useful to utilize filler granules for the tableting process. For this purpose, any pharmaceutically inert granule that is roughly comparable in size to the coated aspirin granules and which will deform or crush in preference to the coated aspirin granules under the compression forces of tableting may be used. It is advantageous to have a sufficient size distribution of the filler granules so as to fill in the interstices and provide a mechanically stable tablet.

To provide filler granules having those characteristics, I have found the following formulation to be particularly advantageous: 340 parts of hydrous lactose USP, 88 parts of microcrystalline cellulose USP, 25 parts of an 11% mixture of sodium carboxymethylcellulose and microcrystalline cellulose, and 39 parts of pregelatinized starch USP/NF bound with 18 parts of USP 2910 HPMC 15 cps. The microcrystalline cellulose USP of preferred 50 μm average particle size is commercially available from FMC as Avicel® PH101. The microcrystalline cellulose containing 11+/−2.7% carboxymethylcellulose is available from FMC as Avicel® RC-581. The pregelatinized starch is available from Colorcon Inc. (U.S.A.). The hydroxypropylmethylcellulose 15 cps is available from Dow Chemical Company (U.S.A.) as Methocel® E and from Shin-etsu (Japan), as Pharmacoat® 615. Alternatively, one may utilize a commercially available filler granule such as Ludipress®. (BASF), a lactose/PVP/crospovidone granule of particle size about 100 to 400 μm.

A preferred embodiment of the tablet consists of 219 mg of the filler granules described above, 92.4 mg of the coated aspirin granules described above, 13.4 mg of sodium starch glycolate, 3.35 mg of talc USP/NF, and 6.7 mg of stearic acid USP/NF. The sodium starch glycolate is commercially available from Generichem (U.S.A.) as Primogel® or from Mendel (U.S.A.) as ExploTab®.

Although not necessary to the practice of the invention, the tablets may have a film coating to minimize mechanical breakdown and provide a more readily swallowed dosage form for the patient. Any film coating that would minimize mechanical breakdown and provide a readily swallowed dosage form without interfering with the release kinetics of the particles or the disintegration rate of the tablet in the stomach would be suitable. However, I have found a coating consisting of about 62 parts of USP 2910 hydroxypropylmethylcelluose of 6 cps viscosity, about 12 parts of polyethylene glycol (PEG) 8000 USP/NF, about 21 parts of titanium dioxide USP, and about 4 parts of talc USP, to be particularly advantageous when applied at a rate of about 10 mg per tablet. When this film coating is applied, a preferred tablet of the invention is obtained; it contains about 75 mg of aspirin, about 8.5 mg of acrylate copolymer, about 0.56 mg of sodium chloride, about 9.2 mg of hydroxypropylmethylcellulose, about 5.6 mg of 500 mesh (3 μm) talc, about 146 mg of lactose, about 38 mg of microcrystalline cellulose, about 11 mg of 11% sodium carboxymethylcellulose in microcrystalline cellulose, about 10 mg of pregelatinized starch, and about 13 mg of sodium starch glycolate, and is coated with about 6.25 mg of HPMC, about 1.22 mg of PEG 8000, about 2.13 mg of titanium dioxide, and about 0.4 mg of talc.

In a process aspect the invention resides in a process for preparing near-zero-order, controlled-release aspirin granules which comprises the aqueous spray-coating of aspirin granules, preferably of particle size 0.5 to 1.5 mm, with a suspension of about 40 to about 60, preferably about 48, parts of a 70:30 copolymer of ethyl acrylate and methyl methacrylate of molecular weight 800,000; about 10 to about 20, preferably about 16, parts of USP 2910 HPMC, preferably of 6 cps HPMC; about 1 to about 12, preferably about 3.2 parts of sodium chloride; and from about 20 to about 45, preferably about 32, parts of talc, preferably having a median particle size of about 3 μm; in about 200 to about 900, preferably about 396, parts of water. The process provides a controlled-release coating that, after drying, constitutes from about 10 to about 35%, preferably about 20%, of the weight of the granule.

In a further process aspect the invention relates to a process for preparing a rapidly-disintegrating, low-dose, controlled-release aspirin tablet. The process comprises the steps of (1) preparing coated aspirin granules by dissolving about 10 to about 20 USP 2910 hydroxypropylmethylcellulose of 3 to 15 cps viscosity in about 90 to about 180 parts of water, suspending about 20 to about 45 parts of talc USP having a median particle size of 3 μm in a solution of about 1 to about 12 parts of sodium chloride in about 40 to about 80 parts of water, combining both with about 130 to about 200 parts of a 30% aqueous emulsion of a 70:30 copolymer of ethyl acrylate and methyl methacrylate and applying the coating mixture to about 580 parts of 20-30 mesh aspirin granules by a suitable air-suspension coating method to provide discrete, coated granules; (2) providing filler granules that are pharmaceutically inert and roughly comparable in size to the aspirin granules of part (1); (3) compressing a homogenous mixture of about 65 to about 90 parts of said filler granules, about 27 parts of said coated aspirin granules, and such other glidants, disintegrants and processing aids as may be required to produce tablets that disintegrate in less than 15 minutes, that deliver aspirin at a rate of 5 to 15 mg/hr and that contain from about 40 to about 100 mg of aspirin each; and (4) optionally film coating said tablets with a rapidly water-soluble film.

The filler granules may be purchased (e.g. Ludipress ®) or prepared by blending about 340 parts of hydrous lactose USP, about 88 parts of microcrystalline cellulose USP of 50 μm average particle size, about 25 parts of an 11% mixture of sodium carboxymethylcellulose in microcrystalline cellulose, and about 39 parts of pregelatinized starch USP/NF in a fluid bed granulator and applying a binder of about 18 parts of USP 2910 hydroxypropylmethylcellulose of 15 cps viscosity in about 239 parts of water at 35°–50°.

The preferred disintegrant for the production of compressed tablets is about 4 parts of sodium starch glycolate; the preferred glidant is about 2 parts of stearic acid NF; and the preferred processing aid is about 1 part of talc USP.

The preferred film coating process comprises optionally film coating said tablets with a homogenous mixture of about 62 parts of USP 2910 hydroxypropylmethylcellulose of 6 cps viscosity, about 12 parts of polyethylene glycol 8000 USP/NF, about 21 parts of titanium dioxide USP, and about 4 parts of talc USP in about 900 parts of water at about 50°–65° centigrade such that the dry weight of film coat on each tablet is about 10 mg.

The following examples will further illustrate the invention without, however, limiting it thereto.

EXAMPLE 1

A 10% solution of hydroxypropylmethylcellulose (HPMC) was prepared by heating 4.952 L of water to 70° C. and adding 1.238 kg of HPMC 2910 (6 cps) with agitation. A second 4.952 L of cold water was added, and stirring was continued until a lumpfree solution was obtained. The solution was allowed to dearate and cool to room temperature. To 12.10 L of water was added 0.2475 kg sodium chloride. When the sodium chloride had dissolved, 2.475 kg of talc USP 3 μm was added with stirring to form a uniform dispersion. 12.38 kg of Eudragit ® NE 30 D was passed through a 40 mesh screen into a suitable container and the deaerated, cooled 10% HPMC solution was added with moderate agitation, followed by the talc/sodium chloride dispersion. The mixture was stirred for at least 30 minutes prior to coating. Mild agitation was maintained during the coating process.

A Glatt CPCG-60 fluidized bed coater, equipped with an 18" Wurster column, was preheated to about 45° C. The column was charged with 33 kg of 20–30 mesh aspirin granules and fluidized to an appropriate level (500–600 cu. ft./minute). 38.35 kg of the coating suspension prepared as above was applied through a 1.2 mm nozzle (atomized by 2.0 bar air pressure) at a rate of 160–200 gram per minute to maintain a product temperature of about 25° C. When the coating suspension was completely consumed, the inlet air temperature was increased to 55° C. and the material was dried and cured for 60 minutes. The coated granules were discharged from the fluid bed, passed through a 16 mesh screen as a check for agglomerates, and stored until needed for tableting.

EXAMPLE 2

Preparation Of The Tablets

Fluid bed preparation of filler granules

A 7% hydroxypropylmethylcellulose binder solution was prepared by heating 30 kg of water to 70° C. and adding 3.00 kg of HPMC 2910 (15 cps) with rapid agitation. Ten kg of cold water was added and the mixing was continued until a lump-free solution was obtained. The solution was allowed to deaerate and cool to below 35° C. 55.2 kg of lactose, 14.4 kg of microcrystalline cellulose, 4.0 kg of Avicel ® RC 581, (an 11% mixture of sodium carboxymethyl cellulose in microcrystalline cellulose) and 6.4 kg pregelatinized starch 1500 were separately passed through a 20 mesh stainless steel screen to remove any large particles. A fluid bed granulator (Glatt GPCG-60) was heated to 40° C. and the lactose, microcrystalline cellulose, Avicel ® RC 581, and starch 1500 were transferred into the preheated granulator. The material was fluidized for 2 minutes and the HPMC binder solution was applied at 650–850 g per minute through three 1.8 mm nozzles with an inlet air temperature of 35°–50° C. When the application was complete, the product was dried at 80° C. until a "loss on drying" test showed less than 3% moisture. After drying, the filler granules were passed through a 14 mesh screen and stored until needed for tableting.

Tableting 5.44 kg of sodium starch glycolate [Explotab ® Low pH] was passed through a 30 mesh screen to remove agglomerates and then combined with 37.5 kg of coated aspirin granules from Example 1 and 88.9 kg of filler granules. The mixture was blended in a twin shell blender for 10 minutes and 1.36 kg of USP talc that had been put through a 60 mesh screen was added and blended 4 or 5 minutes. 2.72 kg of stearic acid USP was passed through a 60 mesh screen, added to the mixture, and blended for a further 5 minutes. The mixture was compressed into tablets on a Manesty Betapress ® with ⅜" standard concave tooling to produce tablets weighing 335+/−10 mg, having a hardness of 3 to 10 KP and a thickness of 0.175 inches +/−0.005 inches.

Film Coating 12.8 L of water was heated to 70° C. and 522 g of polyethylene glycol 8000 USP (Carbowax ® 800) was added with stirring, followed by 2.68 kg of hydroxypropylmethylcellulose 2910 6 cps (Pharmacoat ® 606). Agitation was continued and 25.7 liters of cold water was added. A portion of the solution was combined with 912 g of titanium dioxide USP and passed through an Eppenbach homogenizing mill at 0.005 inches to disperse and homogenize the mixture. The homogenized mixture was reunited with the remaining solution and mixed. 132 kg of uncoated tablets was placed in a 48 inch coating pan (Accela Cota ®) and preheated to 40°–50° C. The film coating was sprayed through two guns, nozzle size 0.043 inch, needle 0.033 inch, at 175 to 225 g per minute continuously through each gun, onto the tablets which were rotated at 9 to 12 rpm with inlet air at 50° to 65° C. at 2,000 cubic feet per minute. A film of approximately 10 mg per tablet was applied to yield tablets having a weight of 345+/−10 mg.

EXAMPLE 3

Analytical Determination Of Release Rate From Granules

Figure 2:
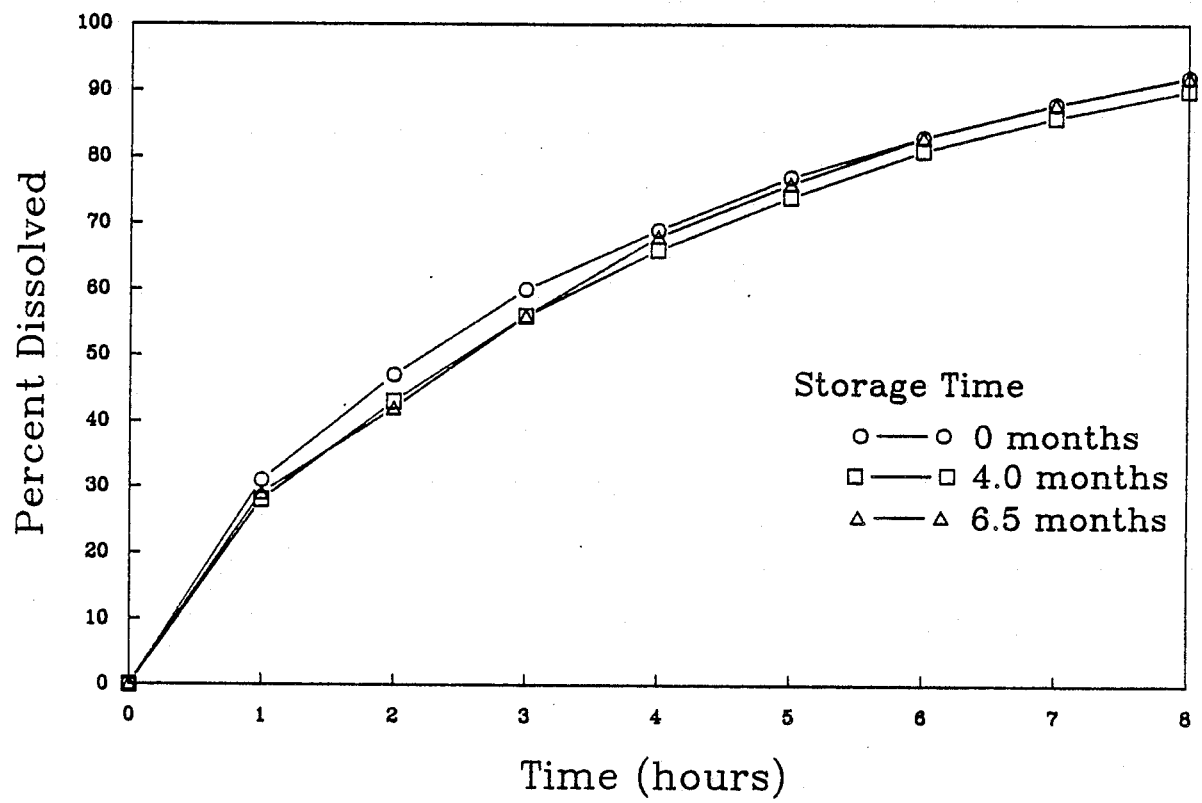
FIG. 2 shows the release of aspirin in percent release plotted against time in hours for the granules of Example 1 as initially prepared and after storage at room temperature for four months and six and one-half months.
Figure 3:
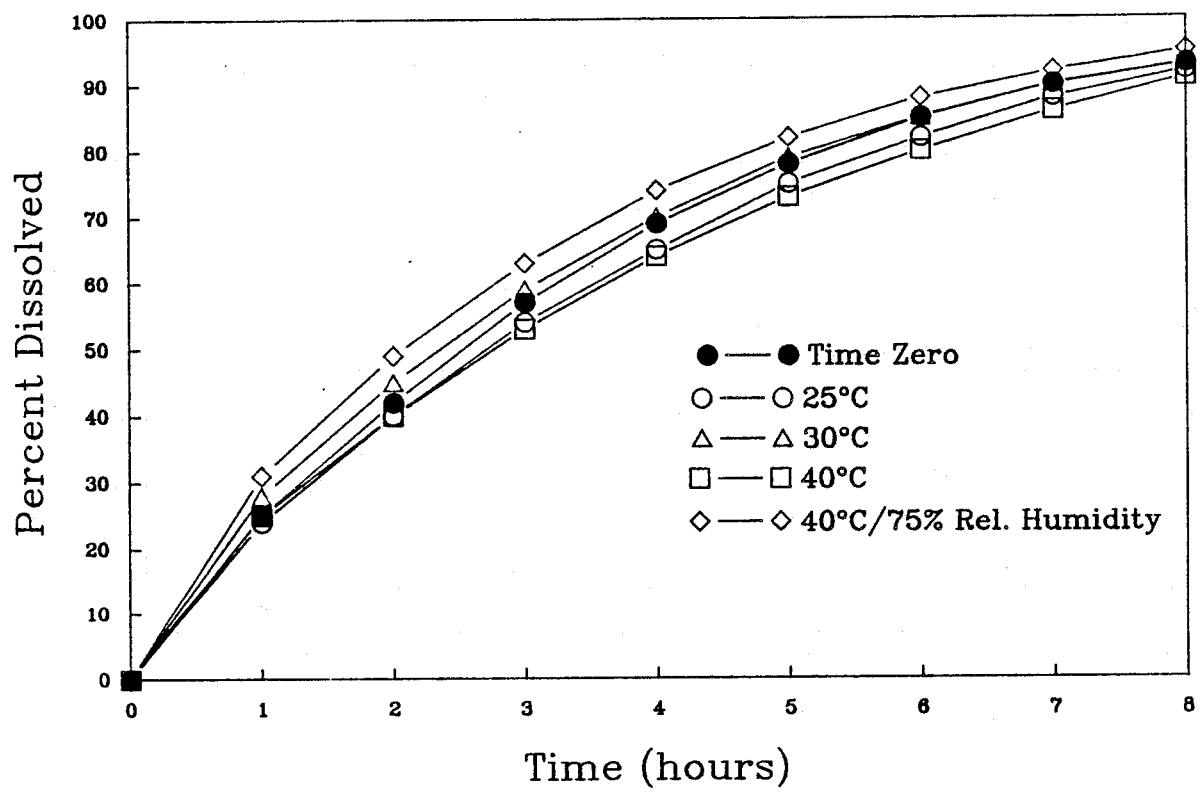
FIG. 3 shows the release of aspirin in percent released plotted against time in hours for the granules of Example 1 after storage for three months at 25°, 30°, 40° C., at ambient humidity and 40° C. at 75% relative humidity. Ambient humidity is maintained at 35–50% relative humidity at 25° C.

The general method and apparatus used are described in USP XXI (711) apparatus 2, rotating paddle. A buffer of pH 6.0 was prepared from 1600 mL of water, 13.5 mL of 85% phosphoric acid and 15.12 g of sodium chloride adjusted to pH 6.0+/−0.05 with 5N sodium hydroxide. A standard was prepared by dissolving 50 mg of aspirin in 1 mL of ethanol and diluting to 100 mL with pH 6.0 buffer. To prepare a standard dilution of about 0.15 mg aspirin per mL, 15.0 mL of the foregoing solution was diluted to 50 mL with pH 6.0 buffer. The assay was carried out in 500 mL of pH 6.0 buffer at 37°+/−0.5° with a paddle stirring speed of 100 rpm. A granule sample equivalent to 75 mg of aspirin was introduced into the apparatus and 10.0 mL aliquots were removed at 1 hour intervals over a period of 8 hours. The quantity of aspirin in the aliquot was determined by spectrophotometric comparison with the standard dilution in 1 cm at 266 nm. FIG. 1 shows a plot of % released versus time in hours for the granules of Example 1. The release profile was not significantly different at pH 1, 4.5, or 7.4. FIGS. 2 and 3 show a plot of % released versus time for the granules of Example 1 after storage under various conditions for different times.

EXAMPLE 4

Analytical Determination Of Release Rate From Tablets

The method described in Example 3, was used but the granule sample was replaced by a tablet containing 75 mg of aspirin. The resulting curve derived from tablets according to Example 2 is shown in FIG. 1.

EXAMPLE 5

Analytical Determination of The Disintegration Rate Of Tablet

The disintegration rate of a tablet prepared according to Example 2 was analyzed using the procedure of USP XXI (701) using the disk method and water as the emersion fluid. The disintegration time of tablets prepared according to Example 2 is less than 5 minutes.

I claim:

1. An aqueous-based formulation for coating aspirin granules to provide coated granules that may be compressed into tablets and that show approximately zero-order release kinetics for release rates of 5 to 15 mg/hr over a period extending five to eight hours, said formulation consisting essentially of (a) from about 40 to about 60 parts of a 70:30 copolymer of ethyl acrylate and methyl methacrylate of average molecular weight 800,000; (b) from about 10 to about 20 parts of hydroxypropylmethyl cellulose of ASTM viscosity 3 to 15 cps and having a hydroxypropyl content of 7 to 12 weight percent and a methoxyl content of 28 to 30 weight percent; (c) from about 1 to about 12 parts of sodium chloride; (d) from about 20 to about 45 parts of talc USP; and (e) from about 200 to about 900 parts of water.

2. A formulation according to claim 1 consisting essentially of about 48 parts of said acrylate copolymer, about 16 parts of hydroxypropylmethylcellulose of ASTM viscosity 6 cps, about 3.2 parts of sodium chloride, about 32 parts of said talc of median particle size 3 μm; and about 396 parts of water.

3. A controlled-release aspirin granule of particle size 0.5 to 1.5 mm coated with 10 to 35% on a dry weight basis of a formulation according to claim 1.

4. A controlled-release aspirin granule of particle size 0.5 to 1.5 mm coated with about 20% on a dry weight basis of a formulation according to claim 2.

5. A rapidly disintegrating, low-dose, controlled-release aspirin tablet comprising from 40 to 100 mg of aspirin granules coated with the coating of claim 1.

6. An aspirin tablet according to claim 5 that disintegrates within 15 minutes and provides a release rate of aspirin of about 5 to about 15 mg per hour.

7. A tablet according to claim 6 comprising about 75 mg of aspirin, about 8.5 mg of said acrylate copolymer, and about 0.56 mg of sodium chloride.

8. A tablet according to claim 7 further comprising about 219 mg of filler granules.

9. A tablet according to claim 7 comprising about 75 mg of aspirin, about 8.5 mg of said acrylate copolymer, about 0.56 mg of sodium chloride, about 9.2 mg of hydroxypropylmethylcellulose, about 5.6 mg of talc of median particle size 3 μm, about 146 mg of lactose, about 38 mg of microcrystalline cellulose, about 11 mg of 11% sodium carboxymethylcellulose in microcrystalline cellulose, about 10 mg of pregelatinized starch, and about 13 mg of sodium starch glycolate.

10. A process for preparing near-zero-order, controlled-release aspirin granules which comprises the aqueous spray-coating of aspirin granules with a suspension of about 40 to about 60 parts of a 70:30 copolymer of ethyl acrylate and methyl methacrylate of molecular weight 800,000, about 10 to about 20 parts of USP 2910 hydroxypropylmethylcellulose, about 1 to about 12 parts of sodium chloride and about 20 to about 45 parts of talc in about 200 to about 900 parts of water.

11. A process according to claim 10 wherein the total weight of dry solids spray-coated onto said aspirin granules is from about 10 to about 35% of the weight of said granules.

12. A process according to claim 11 wherein the total weight of dry solids is about 20% of the weight of said aspirin granules.

13. A process for preparing a low-dose, rapidly disintegrating, controlled-release aspirin tablet which comprises the steps of:

(1) preparing coated aspirin granules by dissolving about 10 to about 20 parts of USP 2910 hydroxypropylmethylcellulose of 3 to 15 cps viscosity in about 90 to about 180 parts of water, suspending about 20 to about 45 parts of talc USP having a median particle size of 3 μm in a solution of about 1 to about 12 parts of sodium chloride in about 40 to about 580 parts of water, combining both with about 130 to about 200 parts of a 30% aqueous emulsion of a 70:30 copolymer of ethyl acrylate and methyl methacrylate and applying the coating mixture to about 580 parts of 20-30 mesh aspirin granules by a suitable air-suspension coating method to provide discrete, coated granules;

(2) providing filler granules that are pharmaceutically inert and roughly comparable in size to the aspirin granules of part(1); and (3) compressing a homogenous mixture of about 65 to about 90 parts of said filler granules, about 27 parts of said coated aspirin granules, and such other glidants, disintegrants and processing aids as may be required to produce tablets that disintegrate in less than 15 minutes, that deliver aspirin at a rate of 5 to 15 mg/hr and that contain from about 40 to about 100 mg of aspirin each.

14. A process for preparing a low-dose, rapidly disintegrating, controlled-release aspirin tablet which comprises the steps of:
  (1) preparing coated aspirin granules by dissolving about 10 to about 20 parts of USP 2910 hydroxypropylmethylcellulose of 3 to 15 cps viscosity in about 90 to about 180 parts of water, suspending about 20 to about 45 parts of talc USP having a median particle size of 3 $\mu$m in a solution of about 1 to about 12 parts of sodium chloride in about 40 to about 580 parts of water, combining both with about 130 to about 200 parts of a 30% aqueous emulsion of a 70:30 copolymer of ethyl acrylate and methyl methacrylate and applying the coating mixture to about 580 parts of 20-30 mesh aspirin granules by a suitable air suspension coating method to provide discrete, coated granules;
  (2) providing filler granules that are pharmaceutically inert and roughly comparable in size to the aspirin granules of part(1); and
  (3) compressing a homogenous mixture of about 65 to about 90 parts of said filler granules, about 27 parts of said coated aspirin granules, and such other glidants, disintegrants and processing aids as may be required to produce tablets that disintegrate in less than 15 minutes, that deliver aspirin at a rate of 5 to 15 mg/hr and that contain from about 40 to about 100 mg of aspirin each; and
  (4) film coating said tablets with a rapidly water soluble film.

15. A process according to claim 13 for preparing a low-dose, rapidly disintegrating, controlled-release aspirin tablet which comprises the steps of:
  (1) preparing coated aspirin granules by dissolving about 16 parts of USP 2910 hydroxypropylmethylcellulose of 6 cps viscosity in about 144 parts of water, suspending about 32 parts of talc USP having a median particle size of 3 $\mu$m in a solution of about 3.2 parts of sodium chloride in about 140 parts of water, combining both with 160 parts of a 30% aqueous emulsion of a 70:30 copolymer of ethyl acrylate and methyl methacrylate and applying the coating mixture to about 576 parts of 20-30 mesh aspirin granules;
  (2) preparing filler granules by blending about 340 parts of hydrous lactose USP, about 88 parts of microcrystalline cellulose USP of 50 $\mu$m average particle size, about 25 parts of an 11% mixture of sodium carboxymethylcellulose in microcrystalline cellulose, and about 39 parts of pregelatinized starch USP/NF in a fluid bed granulator and applying a binder of about 18 parts of USP 2910 hydroxypropylmethylcellulose of 15 cps viscosity in about 239 parts of water at 35° to 50° C.; and
  (3) compressing a homogenous mixture of about 65 parts of said filler granules, about 27 parts of coated aspirin granules, about 4 parts of sodium starch glycolate USP, about 1 part of talc USP, and about 2 parts of stearic acid NF in a standard tablet press to produce tablets weighing about 335 mg and containing about 75 mg of aspirin each.

16. A process according to claim 14 for preparing a low-dose, rapidly disintegrating, controlled-release aspirin tablet which comprises the steps of:
  (1) preparing coated aspirin granules by dissolving about 16 parts of USP 2910 hydroxypropylmethylcellulose of 6 cps viscosity in about 144 parts of water, suspending about 32 parts of talc USP having a median particle size of 3 $\mu$m in a solution of about 3.2 parts of sodium chloride in about 140 parts of water, combining both with 160 parts of a 30% aqueous emulsion of a 70:30 copolymer of ethyl acrylate and methyl methacrylate and applying the coating mixture to about 576 parts of 20-30 mesh aspirin granules;
  (2) preparing filler granules by blending about 340 parts of hydrous lactose USP, about 88 parts of microcrystalline cellulose USP of 50 $\mu$m average particle size, about 25 parts of an 11% mixture of sodium carboxymethylcellulose in microcrystalline cellulose, and about 39 parts of pregelatinized starch USP/NF in a fluid bed granulator and applying a binder of about 18 parts of USP 2910 hydroxypropylmethylcellulose of 15 cps viscosity in about 239 parts of water at 35° to 50° C.;
  (3) compressing a homogenous mixture of about 65 parts of said filler granules, about 27 parts of said coated aspirin granules, about 4 parts of sodium starch glycolate USP, about 1 part of talc USP, and about 2 parts of stearic acid NF in a standard tablet press to produce tablets weighing about 335 mg and containing about 75 mg of aspirin each; and
  (4) film coating said tablets with a homogenous mixture of about 62 parts of USP 2910 hydroxypropylmethylcellulose of 6 cps viscosity, about 12 parts of polyethylene glycol 8000 USP/NF, about 21 parts of titanium dioxide USP, and about 4 parts of talc USP in about 900 parts of water at about 50°-65° C. such that the final weight of each tablet is about 345 mg.

17. A method for treating or preventing vascular occlusive diseases in humans which comprises orally administering a tablet according to claim 5.

18. A method for treating or preventing vascular occlusive diseases in humans which comprises orally administering a tablet according to claim 6.

19. A method for treating or preventing vascular occlusive diseases in humans which comprises orally administering a tablet according to claim 7.

20. A method for treating or preventing vascular occlusive diseases in humans which comprises orally administering a tablet according to claim 8.

21. A method for treating or preventing vascular occlusive diseases in humans which comprises orally administering a tablet according to claim 9.

* * * * *